(12) United States Patent
Parrish

(10) Patent No.: US 8,951,300 B2
(45) Date of Patent: Feb. 10, 2015

(54) INTERVERTEBRAL DISC SPACER

(76) Inventor: Rob Gene Parrish, Houston, TX (US)

( * ) Notice: Subject to any disclaimer, the term of this patent is extended or adjusted under 35 U.S.C. 154(b) by 0 days.

(21) Appl. No.: 12/012,985

(22) Filed: Feb. 6, 2008

(65) Prior Publication Data

US 2008/0154381 A1    Jun. 26, 2008

Related U.S. Application Data

(62) Division of application No. 11/643,536, filed on Dec. 21, 2006, now abandoned.

(51) Int. Cl.
| | | |
|---|---|---|
| *A61F 2/44* | (2006.01) | |
| *A61F 2/46* | (2006.01) | |
| *A61F 2/28* | (2006.01) | |
| *A61F 2/30* | (2006.01) | |

(52) U.S. Cl.
CPC ............. *A61F 2/442* (2013.01); *A61F 2/4611* (2013.01); *A61F 2002/2817* (2013.01); *A61F 2002/30062* (2013.01); *A61F 2002/30354* (2013.01); *A61F 2002/30563* (2013.01); *A61F 2002/30568* (2013.01); *A61F 2002/30571* (2013.01); *A61F 2002/30787* (2013.01); *A61F 2002/444* (2013.01); *A61F 2002/4475* (2013.01); *A61F 2002/4627* (2013.01); *A61F 2002/4629* (2013.01); *A61F 2210/0004* (2013.01); *A61F 2220/0033* (2013.01)
USPC ..................................... 623/17.11; 623/17.16

(58) Field of Classification Search
CPC ... A61F 2/44; A61F 2220/0025; A61F 2/442; A61F 2002/30565; A61F 2002/30566; A61F 2002/30571
USPC ............. 623/17.11–17.16; 606/246–249, 279
See application file for complete search history.

(56) References Cited

U.S. PATENT DOCUMENTS

| | | | |
|---|---|---|---|
| 4,772,287 A | 9/1988 | Ray et al. | |
| 4,904,260 A | 2/1990 | Ray et al. | |
| 6,231,609 B1 * | 5/2001 | Mehdizadeh | ............... 623/17.11 |
| 6,293,949 B1 | 9/2001 | Justis et al. | |
| 6,409,765 B1 | 6/2002 | Bianchi et al. | |

(Continued)

OTHER PUBLICATIONS

Eric Steck, Helge Bertram, Rainer Abel, Bohua Chen, Anja Winter, Willtrud Richter,, "Induction of Intervertebral Disc-Like Cells From Adult Mesenchymal Stem Cells" www.StemCells.com, Nov. 2006.

(Continued)

*Primary Examiner* — Mary Hoffman
*Assistant Examiner* — Christina Negrellirodriguez

(57) ABSTRACT

Methods and devices are provided for improving the stability, flexibility, and/or proper anatomical motion of a spinal column and more particularly, spinal implant devices are provided for use between adjacent vertebral bones. Intervertebral disc spacer devices may comprise two joined surfaces formed of compressible materials. The surfaces may be convex or any variety of shapes. Certain embodiments of intervertebral disc spacer devices include apertures through which nutrients may pass. Additionally, certain embodiments include a partial enclosure or open region between the two surfaces so as to provide an environment conducive to regrowth or stimulation of natural intervertebral disc material. In certain embodiments, the two surfaces may be attached by one or more springs. Alternatively, intervertebral disc spacer embodiments may be comprised of a coiled wire. Methods of introducing intervertebral disc spacer devices into patients are also provided.

7 Claims, 6 Drawing Sheets

(56) References Cited

U.S. PATENT DOCUMENTS

| | | |
|---|---|---|
| 6,454,806 B1 | 9/2002 | Cohen et al. |
| 6,461,359 B1 | 10/2002 | Tribus et al. |
| 6,464,727 B1 | 10/2002 | Sharkey et al. |
| 6,468,309 B1 * | 10/2002 | Lieberman ............... 623/17.11 |
| 6,468,310 B1 | 10/2002 | Ralph et al. |
| 6,478,823 B1 | 11/2002 | Michelson |
| 6,602,291 B1 | 8/2003 | Ray et al. |
| 6,610,092 B2 | 8/2003 | Ralph et al. |
| 6,610,093 B1 | 8/2003 | Pisharodi |
| 6,683,192 B2 | 1/2004 | Baxter et al. |
| 6,689,125 B1 | 2/2004 | Keith et al. |
| 6,695,882 B2 | 2/2004 | Bianchi et al. |
| 6,699,294 B2 | 3/2004 | Urry |
| 6,706,005 B2 | 3/2004 | Roy et al. |
| 6,719,796 B2 | 4/2004 | Cohen et al. |
| 6,740,119 B2 | 5/2004 | Ralph et al. |
| 6,743,257 B2 | 6/2004 | Castro |
| 6,758,861 B2 | 7/2004 | Ralph et al. |
| 6,770,074 B2 | 8/2004 | Michelson |
| 6,783,546 B2 | 8/2004 | Zucherman et al. |
| 6,805,695 B2 | 10/2004 | Keith et al. |
| 6,805,715 B2 | 10/2004 | Reuter et al. |
| 6,814,737 B2 | 11/2004 | Cauthen |
| 6,833,006 B2 | 12/2004 | Foley et al. |
| 6,869,446 B2 | 3/2005 | Ralph et al. |
| 6,887,273 B2 | 5/2005 | Ralph et al. |
| 6,893,465 B2 | 5/2005 | Huang |
| 6,899,716 B2 | 5/2005 | Cragg |
| 6,899,735 B2 | 5/2005 | Coates et al. |
| 6,911,045 B2 | 6/2005 | Shimp |
| 6,913,622 B2 | 7/2005 | Gjunter |
| 6,932,844 B2 | 8/2005 | Ralph et al. |
| 6,964,665 B2 | 11/2005 | Thomas et al. |
| 6,966,910 B2 | 11/2005 | Ritland |
| 6,989,032 B2 | 1/2006 | Errico et al. |
| 7,001,431 B2 | 2/2006 | Bao et al. |
| 7,014,633 B2 | 3/2006 | Cragg |
| 7,052,516 B2 | 5/2006 | Cauthen, III et al. |
| 7,063,725 B2 | 6/2006 | Foley |
| 7,066,939 B2 | 6/2006 | Taylor |
| 7,066,958 B2 | 6/2006 | Ferree |
| 7,066,959 B2 | 6/2006 | Errico et al. |
| 7,066,960 B1 | 6/2006 | Dickman |
| 7,066,961 B2 | 6/2006 | Michelson |
| 7,070,556 B2 | 7/2006 | Anderson et al. |
| 7,074,201 B2 | 7/2006 | Reinecke et al. |
| 7,074,240 B2 | 7/2006 | Pisharodi |
| 7,077,844 B2 | 7/2006 | Michelson |
| 7,077,866 B2 | 7/2006 | Gresser et al. |
| 7,081,123 B2 | 7/2006 | Merboth et al. |
| 7,083,649 B2 | 8/2006 | Zucherman et al. |
| 7,083,651 B2 | 8/2006 | Diaz et al. |
| 7,083,749 B2 | 8/2006 | Lin et al. |
| 7,087,056 B2 | 8/2006 | Vaughan |
| 7,087,082 B2 | 8/2006 | Paul et al. |
| 7,087,084 B2 | 8/2006 | Reiley |
| 7,090,301 B2 | 8/2006 | Stadlbauer |
| 7,090,698 B2 | 8/2006 | Goble et al. |
| 7,094,237 B2 | 8/2006 | Gradel et al. |
| 7,094,238 B2 | 8/2006 | Morrison et al. |
| 7,094,258 B2 | 8/2006 | Lambrecht et al. |
| 7,097,643 B2 | 8/2006 | Cornelius et al. |
| 7,101,375 B2 | 9/2006 | Zucherman et al. |
| 7,101,398 B2 | 9/2006 | Dooris et al. |
| 7,101,399 B2 | 9/2006 | Errico et al. |
| 7,101,400 B2 | 9/2006 | Thramann et al. |
| 7,104,966 B2 | 9/2006 | Shiber |
| 7,104,986 B2 | 9/2006 | Hovda et al. |
| 7,105,011 B2 | 9/2006 | Auge, II |
| 7,105,023 B2 | 9/2006 | Eckman |
| 7,105,024 B2 | 9/2006 | Richelsoph |
| 7,105,029 B2 | 9/2006 | Doubler et al. |
| 7,108,671 B2 | 9/2006 | Saunders et al. |
| 7,108,714 B1 | 9/2006 | Becker |
| 7,108,862 B2 | 9/2006 | Remington et al. |
| 7,109,181 B2 | 9/2006 | Cowlen et al. |
| 7,111,402 B1 | 9/2006 | Pearman |
| 7,111,692 B2 | 9/2006 | Hosie et al. |
| 7,112,206 B2 | 9/2006 | Michelson |
| 7,112,222 B2 | 9/2006 | Fraser et al. |
| 7,112,417 B2 | 9/2006 | Vyakarnam et al. |
| 7,114,501 B2 | 10/2006 | Johnson et al. |
| 7,115,132 B2 | 10/2006 | Errico et al. |
| 7,115,144 B2 | 10/2006 | Diaz et al. |
| 7,115,653 B2 | 10/2006 | Baxter et al. |
| 2004/0002761 A1* | 1/2004 | Rogers et al. .............. 623/17.13 |
| 2005/0027364 A1* | 2/2005 | Kim et al. .................. 623/17.13 |
| 2005/0113924 A1* | 5/2005 | Buttermann ............... 623/17.13 |
| 2006/0085009 A1* | 4/2006 | Truckai et al. .................. 606/94 |
| 2006/0149380 A1* | 7/2006 | Lotz et al. .................. 623/17.12 |

OTHER PUBLICATIONS

Charles D. Ray, "The PDN prosthetic disc-nucleus device" Jun. 2002.

A. Korge, TH. Nydegger, J.L. Polard, H.M. Mayer, J.L. Husson, "A spiral implant as nucleus prosthesis in the lumbar spine" Aug. 2002. Neorosurg Focus, vol. 13, Aug. 2002, "Alternatives to lumbar discectomy".

J.L. Husson, A. Korge, J.L. Polard, TH. Nydegger, S. Kneubuhler, and H.M. Mayer, "A Memory Coiling Spiral as Nucleus Pulposus Prosthesis," J. Spinal Disord & Techniques, vol. 16, No. 4, 2003.

* cited by examiner

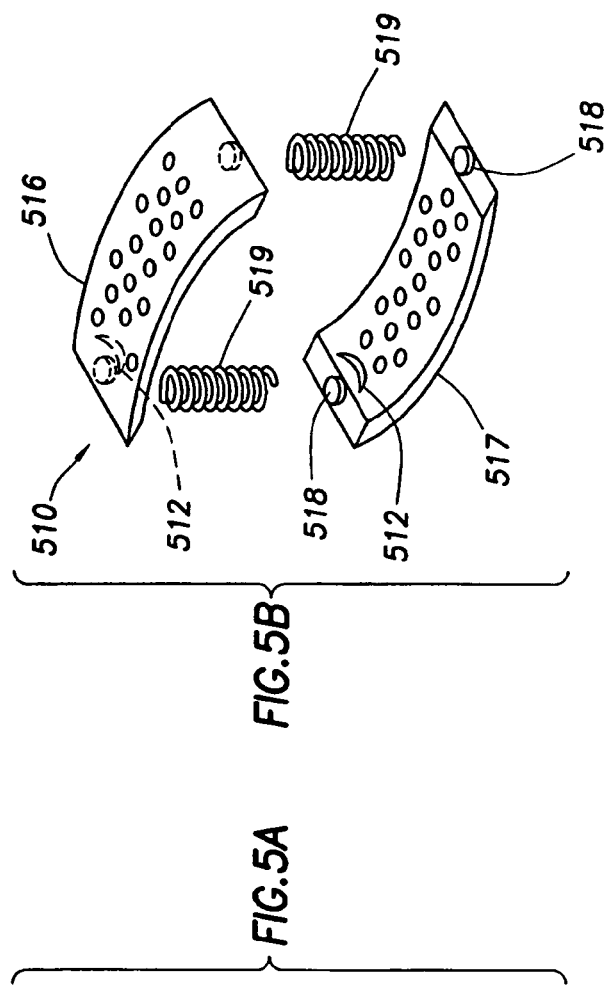
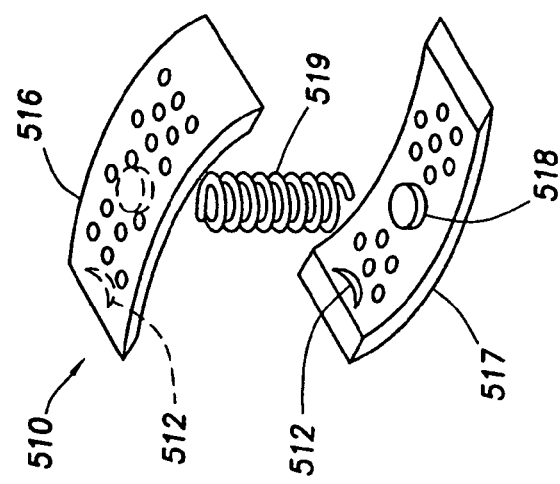
FIG.5B
FIG.5A

INTERVERTEBRAL DISC SPACER

CROSS-REFERENCE TO RELATED APPLICATION

The present application is a divisional of and claims priority to U.S. patent application Ser. No. 11/643,536, filed Dec. 21, 2006, now abandoned entitled "Intervertebral Disc Spacer," the entirety of which is hereby incorporated by reference.

BACKGROUND

The present invention generally relates to methods and devices for improving the stability, flexibility, and/or proper anatomical motion of a spinal column and more particularly, to spinal implant devices for use between adjacent vertebral bones.

The normal human spine contains 23 moveable intervertebral discs located between the adjacent vertebral body endplates of the spine. These discs form an important part of the articulating systems of the spine, allowing for complex motion. In general, the discs permit movements such as flexion, extension, lateral flexion, and rotation. Discs are living tissue but have no blood supply. Disc tissues are sustained by an exchange of waste products and nutrients with surrounding vascular tissues. This exchange is augmented by increases and decreases in pressures within the disc tissues.

Intervertebral discs undergo anatomical changes including degeneration due to natural aging processes and due to injury. Disc degeneration is a progressive process and can include a decrease in the water and proteoglycan content of the nucleus pulposus and the annulus, distortion of the collagen fibers of the annulus fibrosus, and tears in the lamellae.

Disc degeneration is problematic, because degeneration of the intervertebral discs reduces the ability of the discs to perform their various functions such as absorbing and distributing load forces of the spine vertebrae. Essentially, the degenerated discs no longer function as effectively as shock absorbers. Additionally, disc degeneration can result in narrowing of the invertebral spaces, resulting in additional stresses to other spinal components, particularly the ligaments of the spine. Narrowing of the intervertebral disc spaces can also result in spinal segment instabilities. In more serious cases of disc degeneration, a disc can become wholly degenerated resulting in adjacent spinal vertebrae coming in contact with one another, a painful condition associated with numerous adverse and serious complications of the spine. All of these changes can lead to abnormal motion of spinal segments and pain during normal physiological movements.

Intervertebral disc degeneration is treated with many modalities, including methods that focus on disc replacement, regrowth or stimulation of the degenerated discs, and spinal immobilization and stabilization devices. Surgery is often employed in extreme cases when instability or pain develops or when there is a compromise of neural elements of the spine. Historically, surgery has been designed to remove degenerative discs, modify the anatomy of the spine to accommodate the degenerative processes, replace disc components with synthetic material, or fuse adjoining vertebrae to prevent painful movement.

One example of a disc replacement device is the "Fernstrom ball," which is essentially a ball placed in between vertebrae to maintain an appropriate height between the vertebrae. Such disc replacement devices suffer from a variety of disadvantages including subsidence of the device into vertebral end plates. In other words, over time, the ball can poke through and into the adjacent vertebrae thus losing any increase in height of the disc space. The "Fernstrom ball" is also rigid and acts as a barrier to the disc tissues from the needed changes in intradiscal pressure needed to sustain living cells. The "Fernstrom ball" is usually made of steel, which can have adverse reactions with tissues and whose trace metals may interfere with cell proliferation and rejuvenation.

Regeneration of discs may be facilitated by the transplant of more normal disc material from adjacent healthier discs, autologous grafts, and/or by the introduction of growth factors or other stimulants to aid in disc regeneration. For example, one author proposes the use of adult mesenchymal stem cells to stimulate regrowth of intervertebral discs. See, e.g., Steck et al., *Induction of Intervertebral Disc-Like Cells from Adult Mesenchymal Stem Cells,* 23 STEM CELLS 403-411 (2005). Because of the early stage of some of these methods however, this solution is not ideal for all degenerative disc problems. Furthermore, in the degenerative disc, compensatory anatomical changes may have taken place. Loss of elasticity and compressibility coupled with Modic changes in adjacent bony endplates may predispose the discs to further deterioration. Adjacent ligaments may have contracted and thickened, further isolating disc tissues from necessary nutrients.

Another approach uses immobilization devices to isolate and stabilize the vertebrae affected by the degenerated intervertebral disc. Some of these devices use bolts and screws to immobilize adjacent vertebrae of the spine. This solution suffers from a number of disadvantages including reduced mobility of the spine. Additionally, immobilizing two adjacent vertebrae has the disadvantage of transferring stresses to adjoining levels of vertebrae thus accelerating the degenerative process in adjacent vertebrae. Physiologic motion is lost with frequent decreases in activity level to include vocational and recreational practices.

Some conventional approaches have proposed replacing the intervertebral disc with a synthetic device. The synthetic implants suffer from a number of disadvantages. In conventional synthetic implant procedures, all remaining normal disc material is removed and excluded from the disc space. Failed attempts to replace herniated or degenerated nuclei include the concepts of a waterbladder (See U.S. Pat. No. 3,875,595), a hydrophilic elastomer (See Edeland, *Suggestions for a total elasto-dynamic intervertebral disc prosthesis,* 9 BIOMATER. MED. DEV. ARTIF. ORGANS 65-72 (1981)), and a silicone polyethylene implant (See Edeland, *Some Additional Suggestions for an intervertebral disc prosthesis,* 8 J. BIOMED. MATER. RESOURCES APPL. BIOMATER. S36-S37 (1989)). Other reported problems of synthetic implants such as the one disclosed in Ray, *The PDN® Prosthetic Disc-Nucleus Device,* 11 (Suppl. 2) EUR. SPINE J. S137-142 (2002), include difficulties in implantation techniques as well as reports of implant dislocations. Some of the prior art synthetic disc replacement devices heretofore proposed have taught that the replacement device should be rigid and/or not compressible. By not being compressible, the rigid prior art disc replacement devices fail to adequately perform the natural functions of intervertebral discs, including acting as a shock absorber to absorb and distribute the forces imposed by the vertebrae.

Although a variety of solutions have been proposed to address the problem of invertebral disc degeneration, the prior art solutions to the problem of degenerative discs heretofore proposed suffer from one or more disadvantages, including among others, failing to provide an environment conducive to regeneration of normal intervertebral disc material, failing to restore normal intervertebral disc function, and/or failing to sustain normal physiological function of the person and biological function of the disc itself.

SUMMARY

The present invention generally relates to methods and devices for improving the stability, flexibility, and/or proper anatomical motion of a spinal column and more particularly, to spinal implant devices for use between adjacent vertebral bones.

An example of one embodiment of an intervertebral disc spacer comprises a first surface formed of a compressible material, the first surface having a first end and a second end; a second surface formed of a compressible material, the second surface having a first end and a second end; wherein at least a portion of the first end of the first surface is attached to at least a portion of the first end of the second surface and at least a portion of the second end of the second surface is attached to at least a portion of the second end of the second surface so as to define a region capable of at least partially enclosing an intervertebral disc; and wherein the first surface and the second surface include a plurality of apertures through which nutrients may pass.

Another example of an embodiment of an intervertebral disc spacer for stabilizing a portion of a spinal column having a plurality of intervertebral spaces comprises a first surface; a second surface; and a spring having a first end and a second end, wherein the first end of the spring is engaged with the first surface and wherein the second end of the spring is engaged with the second surface.

An example of a device for stabilizing a portion of a spinal column having a plurality of intervertebral spaces comprises a coiled wire having a diameter from about 0.5 mm to about 2 mm for placement in one of the intervertebral spaces wherein the coiled wire is formed of an inert biocompatible and elastic material.

Examples of methods for stabilizing a portion of a spinal column may comprise the steps of: introducing an intervertebral disc spacer between two vertebrae using an introducer tool; wherein the intervertebral disc spacer comprises a first surface formed of a compressible material, the first surface having a first end and a second end, a second surface formed of a compressible material, the second surface having a first end and a second end, wherein at least a portion of the first end of the first surface is attached to at least a portion of the first end of the second surface and at least a portion of the second end of the second surface is attached to at least a portion of the second end of the second surface so as to define a region capable of at least partially enclosing an intervertebral disc, and wherein the first surface and the second surface include a plurality of apertures through which nutrients may pass; and placing the intervertebral disc spacer between two vertebrae.

Advantages of various embodiments of the present invention include in part the restoration of a more normal anatomy than that of a degenerative disc. The restoration may be accomplished by increasing the height of the disc space (i.e. the space between adjacent vertebral bodies). This increased space opens in turn the neural foramen that is often made smaller in the degenerative spine, thus relieving compression on the neural elements. Increasing the disc space height also stretches surrounding ligaments leading to a more stable spine. The ligaments dorsal to the spinal canal are also stretched to a more normal length, increasing the effective diameter of the spinal canal and relieving compression of neural structures. Thus, certain embodiments of the device maintain or restore normal disc space dimensions to stabilize the spine using natural ligament structures and remove harmful compressive forces or direct stresses on the remaining disc material.

Another advantage of certain embodiments of the present invention is the creation of an environment within the disc space to prevent further disc deterioration and provide an environment that facilitates disc regeneration. Additionally, certain embodiments of the disc spacer of the present invention may be used in conjunction with chemical and physical substances that may be introduced into the disc space to facilitate regeneration of the natural disc material itself.

Certain embodiments of the methods of the present invention are advantageous in that the devices of the present invention may be inserted through minimally invasive techniques such that open surgery is not required, though such surgery may be employed.

The features and advantages of the present invention will be apparent to those skilled in the art. While numerous changes may be made by those skilled in the art, such changes are within the spirit of the invention.

BRIEF DESCRIPTION OF THE DRAWINGS

A more complete understanding of the present disclosure and advantages thereof may be acquired by referring to the following description taken in conjunction with the accompanying figures, wherein:

FIG. 5A illustrates an exploded view of yet another embodiment of an intervertebral disc spacer comprised of a coiled spring.

FIG. 5B illustrates an exploded view of an embodiment of an intervertebral disc spacer having a plurality of springs.

Figure 1A:
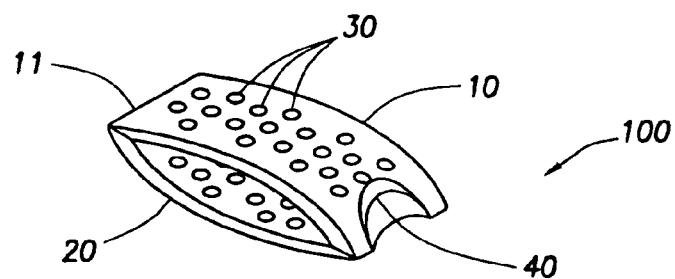
FIG. 1A illustrates a perspective view of one embodiment of an intervertebral disc spacer.

While the present invention is susceptible to various modifications and alternative forms, specific exemplary embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DESCRIPTION OF PREFERRED EMBODIMENTS

The present invention generally relates to methods and devices for improving the stability, flexibility, and/or proper anatomical motion of a spinal column and more particularly, to spinal implant devices for use between adjacent vertebral bones.

In certain embodiments, the intervertebral disc spacer devices of the present invention allow for preservation of spinal function and preservation of the intervertebral disc itself. In particular, certain embodiments of the present invention are permeable thus allowing nutrients and waste material to pass through the intervertebral disc spacer. Additionally, certain embodiments of the present invention have varying degrees of compressibility thus allowing for absorption and distribution of forces exerted by adjacent vertebrae. Other advantages include the ability to prevent further natural disc deterioration and facilitate processes (e.g. endogenous or inserted/implanted/transplanted endogenous or exogenous) designed to re-create a more natural disc. Furthermore, methods of the present invention allow intervertebral disc spacer devices to be inserted into the disc space via minimally invasive techniques, which in some cases do not require open surgical procedures.

To facilitate a better understanding of the present invention, the following examples of certain embodiments are given. In no way should the following examples be read to limit, or define, the scope of the invention.

Figure 1B:
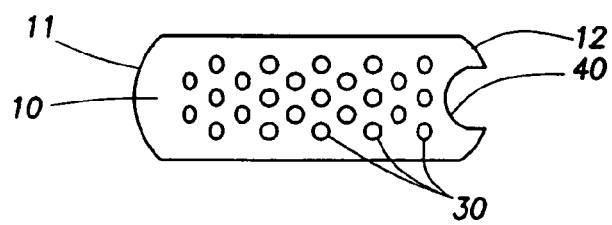
FIG. 1B illustrates a top view of one embodiment of an intervertebral disc spacer.
Figures 1C, 1D:
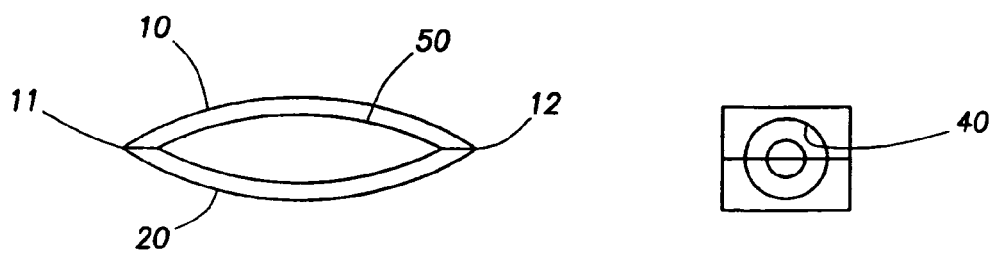
FIG. 1C illustrates a cross-sectional side view of one embodiment of an intervertebral disc spacer.
FIG. 1D illustrates an end view of one embodiment of an intervertebral disc spacer shown from one end having a port for engagement with an introducer tool.

FIGS. 1A, 1B, 1C, and 1D illustrate several views of one embodiment of intervertebral disc spacer 100 for placement between adjacent vertebrae. FIG. 1A illustrates a perspective view of one embodiment of intervertebral disc spacer 100. FIG. 1B illustrates a top view of one embodiment of intervertebral disc spacer 100. FIG. 1C illustrates a cross-sectional side view of one embodiment of intervertebral disc spacer 100.

Generally, intervertebral disc spacer 100 is comprised of first surface 10 attached to second surface 20 so as to create open space 50 between first surface 10 and second surface 20. As explained in more detail below, plurality of apertures 30 in conjunction with open space 50 provides a region conducive the preservation and regrowth of natural disc material therein.

First surface 10 is formed of a compressible material and has first end 11 and second end 12. Second surface 20 is also formed of a compressible material and has a first end 21 and a second end 22. First surface 10 is joined to second surface 20 at first and second ends 11 and 12. First and second surfaces 10 and 20 are formed in such a way that open space 50 is defined between first and second surfaces 10 and 20. Open space 50, as explained in more detail below, allows for a region conducive to the preservation or regrowth of natural disc material. Alternatively, synthetic disc material may occupy open space 50. Examples of synthetic disc material suitable for use in open space 50 includes compressible inert materials that do not cause adverse reactions in the human body, hydrophilic polymers, nonbiodegradable polymers such as polyethylene, biodegradable polymers such as, for example, polyglycolicacid, silicone, any of the materials known in the art for joint replacement, or any combination thereof.

Although each surface of intervertebral disc spacer 100 is depicted as a curved or generally convex band, the shape of intervertebral disc spacer 100 may be any variety of suitable shapes including being substantially disc shaped, substantially in the shape of a rectangle, substantially oblong or spherical, or any shape suitable for maintaining an intervertebral space. In certain embodiments, the contour of each surface 10 and 20 may be irregular to match the contours of adjacent vertebrae. Although in certain embodiments first and second surfaces 10 and 20 are depicted as symmetrical, some embodiments may be asymmetrical such that first surface 10 has a profile different than that of second surface 20.

Intervertebral disc spacer 100 may be composed of any material that does not cause an adverse effect in the human body. Suitable materials include, but are not limited to titanium, nickel/chrome steel, various plastics with adjusted compressibilities such as polyetheretherketones, synthetic materials such as rubber and silicone, and inert materials known in the art for use as internal prosthetic devices, or any combination thereof.

The dimensions of intervertebral disc spacer 100 vary depending on individual patient anatomy and vertebral dimensions. In certain embodiments, the length of each surface 10 and 20 may vary from about 10 to about 30 mm. By way of example, an intervertebral disc spacer for an average male patient for the intervertebral space between lumbar vertebra L-3 and lumbar vertebra L-4 may range from about 25 mm to about 30 mm. Cervical and thoracic vertebrae are much smaller in diameter and thickness.

The width of intervertebral disc spacer 100 also depends on individual patient anatomy and vertebral dimensions. In certain embodiments, the width of each surface 10 and 20 may vary from about 8 to about 25 mm. By way of example, an intervertebral disc spacer for an average male patient for the intervertebral space between lumbar vertebra L-3 and lumbar vertebra L-4 may range from about 8 mm to about 25 mm. An intervertebral disc spacer for an average male patient between lumbar vertebra L-3 and lumbar vertebra L-4 that is inserted through the working space of Kambin may range from about 8 mm to about 16 mm.

The unloaded thickness of the device from the top of first surface 10 to the bottom of second surface 20 varies according to patient anatomy and other factors including the intervertebral height desired. In certain embodiments, the unloaded thickness of the device may range from about 5 mm to about 15 mm for the thoracic or cervical spine and from about 5 mm to about 30 mm in the lumbar spine when the device is under no compression. Once inserted, the thickness of the device will be greater than the insertion thickness and dependent on the load on and the compressibility of the device.

The thickness of first surface 10 and second surface 20 depends on the material used for intervertebral disc spacer 100 and the desired compressibility. The determination of the thickness of intervertebral disc spacer 100 is within the ability of a person of ordinary skill with the benefit of this disclosure.

Other factors that affect the dimensions of intervertebral disc spacer 100 include, but are not limited to, the degree of degeneration leading to surgical intervention, the integrity of vertebral endplates and bone structure, and the activity level of the patient.

Intervertebral disc spacer 100 may be designed with a compressibility sufficient to restore the normal shock absorption and distribution function of an intervertebral disc in the spinal column. Additionally, it is desirable to select a compressibility of a material such that the natural flexing of intervertebral disc spacer 100 will urge fluid flow in and out of open space 50 of intervertebral disc spacer 100. This fluid exchange between open space 50 and the external environment of intervertebral disc spacer 100 aids the passage of nutrients and waste materials in and out of open space 50 so as to provide an environment conducive to the regeneration and/or preservation of natural disc material.

Naturally, the compressibility of intervertebral disc spacer 100 will vary as a function of several variables such as, among others, the location in the spine of intervertebral disc spacer 100, the degree of disc degeneration, the integrity of the annulus, and any material that may be inserted to facilitate disc regeneration. Forces imposed on intervertebral disc spacer 100 typically vary from 0 to about 2,000 Newtons. In certain preferred embodiments, the device should provide some shielding of the disc material from applied forces but not complete shielding. For instance physiological pressures of 3 MPa stimulate synthesis within the disc whereas pressures of 7.5 MPa inhibit synthesis. Accordingly, an optimal elasticity of intervertebral disc spacer 100 should be chosen so as to provide for fluid exchange in and out of intervertebral disc spacer 100 along with an optimal distribution of forces imposed on intervertebral disc spacer 100. In certain embodiments, suitable materials have a Young's Modulus (E) of about 10,000,000 to about 19,000,000 and in other embodiments, from about 15,000,000 to about 17,500,000 psi. Suitable materials may deform up to about 3%, 5%, and 7% in certain instances. Suitable non-metallic materials may have a Young's Modulus (E) of about 430,000 psi to about 10,000,000 psi in certain embodiments.

In certain embodiments, intervertebral disc spacer 100 includes plurality of apertures 30. Apertures 30 may take on a variety of shapes including, but not limited to, circular apertures, cylindrical apertures, rectangular slits, square-shaped apertures, parabolic apertures, elliptical apertures, conical concave or convex apertures, or complex or random shaped apertures. Parabolic holes may provide superior stress distribution on the surface of intervertebral disc spacer 100 in certain embodiments.

The size and concentration of apertures 30 depend on a variety of factors including, but not limited to, desired fluid exchange flow rate, strength of material used, anticipated stresses on intervertebral disc spacer 100, load bearing ability of vertebral end plates. In certain embodiments, apertures 30 vary from microscopic size holes, on the order of about 100 microns to about 500 microns to very porous, on the order of greater than about 2 mm. In certain embodiments, apertures 30 vary from about 1 mm to about 2 mm. Microscopic apertures have the advantage of allowing fluid and cells such as fibroblasts to pass through apertures 30, whereas very porous apertures allow the passage of clumps of tissue to pass through apertures 30. Alternatively, a combination of microscopic apertures and very porous apertures may be used. Thus, one of the advantages of apertures 30 is that they aid in the supply of nutrients and passage of waste materials so as to recreate an environment suitable to encourage regrowth or preservation of natural disc material.

In designing the size and concentration of apertures 30, one should be cognizant of the trade-off between larger apertures and smaller apertures. Larger apertures necessarily have a greater porosity for fluid flow but at the same time provide less surface area for stress distribution of compressive forces. Smaller holes, on the other hand, provide more surface area for stress distribution, but less porosity for fluid exchange. Additionally, as surface area of intervertebral disc spacer 100 increases, the stress distribution of compressive forces increases so as to reduce the problem of subsidence of intervertebral disc spacer 100 into the vertebral end plates by action of forces into adjacent material.

FIG. 1D illustrates an end view of one embodiment of a intervertebral disc spacer 100 shown from one end having a port or notch for engagement with an introducer tool. Port 40 may be provided to allow engagement of an introducer tool for introduction and/or manipulation of intervertebral disc spacer 100. Port 40, although shown here as a cutaway of a portion of first surface 10 and second surface 20 may include any number of features to aid in the engagement of introducer tool to port 40 including, but not limited to, the inclusion of an engagement lip, a screw-type engagement, any engagement mechanism known in the art, or any combination thereof.

Although intervertebral disc spacer 100 is illustrated herein as formed of two separate surfaces 10 and 20, it is recognized that first and second surfaces 10 and 20 may be formed integrally as one piece. That is, the description of intervertebral disc spacer 100 as a first and second surface is intended to include embodiments where first and second surfaces 10 and 20 are formed integrally as one piece. In those embodiments wherein first and second surfaces 10 and 20 are formed of two separate surfaces, first and second surfaces 10 and 20 may be attached by any suitable attachment methods known in the art including, but not limited to, welding, compression bonding, screws, thermal bonding, or any combination thereof.

Figure 2:
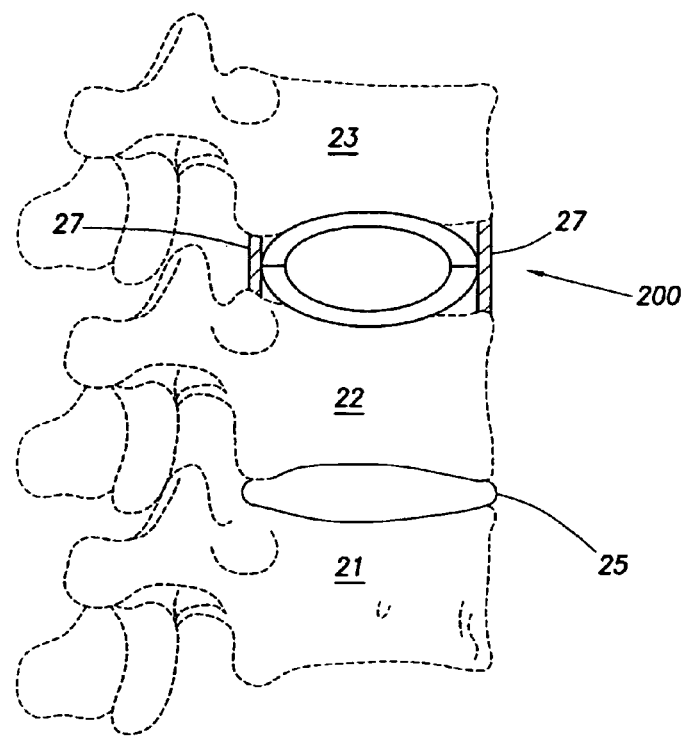
FIG. 2 illustrates another embodiment of a disc spacer wherein the contours of the intervertebral disc spacer have been formed so as to match the contours of adjacent vertebrae and showing the intervertebral disc spacer placed in between the end plates of two adjacent vertebrae.

FIG. 2 illustrates another embodiment of an intervertebral disc spacer showing the intervertebral disc spacer placed in between the end plates of two adjacent vertebrae. Intervertebral disc spacer 200 is shown located between vertebral end plates 22 and 23 and in between end walls of the annulus fibrosus 27. In this environment, compressible intervertebral disc spacer 200 duplicates the function of normal healthy disc 25 by absorbing and redistributing the stress forces imposed by vertebral end plates 22 and 23. Additionally, intervertebral disc spacer 200 provides open space 50 for the preservation or re-growth of natural disc material. In certain embodiments, open space 50 may be used to house a degenerated disc. Additionally, more normal disc material from adjacent healthier discs may be inserted in open space 50. In conjunction with the insertion of natural disc material in open space 50, growth factors and/or other stimulants may be used to aid in disc regeneration. Suitable growth factors and/or other re-growth stimuli include, but are not limited to, portions of growth hormone, viscous cell culture media, proteoglycan (aggrecan) suspension, collagens of various forms, or any combination thereof. Additionally, inhibitors may be introduced into the disc environment to inhibit bone growth. In still other embodiments, a synthetic disc material may be introduced into open space 50. In certain embodiments, however, no disc material is introduced into open space 50 of intervertebral disc spacer 200.

Intervertebral disc spacer 200 may also function to restore the normal height or in some instances, increase the disc space height between vertebral end plates. This increased space opens in turn the neural foramen that is often made smaller in the degenerative spine, thus relieving compression on the neural elements. Increasing the disc space height also stretches surrounding ligaments leading to a more stable spine. The ligaments dorsal to the spinal canal are also stretched to a more normal length, increasing the effective diameter of the spinal canal and relieving compression of neural structures. In this way, intervertebral disc spacer 200 helps to prevent disc deterioration by removing direct stresses upon the disc material itself thus providing an environment more conducive to regeneration of the natural disc material.

FIG. 2 also illustrates an example of an embodiment of an asymmetrical intervertebral disc spacer wherein the top surface of intervertebral disc spacer 200 is not symmetrical with the bottom surface of intervertebral disc spacer 200. In this way, the contours of the intervertebral disc spacer may be formed so as to more closely match the contours of adjacent vertebrae. Accordingly, a greater surface area of intervertebral disc spacer 200 is in contact with the adjacent vertebral end plates thus distributing forces more evenly across vertebral end plates 22 and 23.

Figure 3:
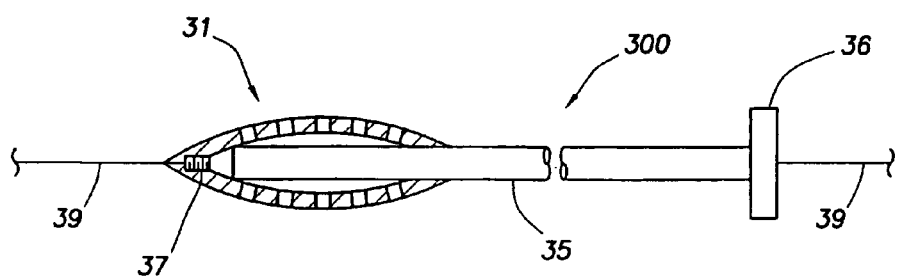
FIG. 3 illustrates a cross-sectional view of an intervertebral disc spacer in cooperation with an introducer tool.

FIG. 3 illustrates a cross-sectional side view of intervertebral disc spacer 31 (IVDS) in cooperation with introducer tool 300. IVDS 30 is attached to the tip of introducer tool 300 by an engagement means 37 such as a screw or a bayonet type connection. Introducer tool 300 traverses the entire length of IVDS 31 such that IVDS 31 is stabilized relative to the long axis of introducer tool 300 and the rotational axis as well. A longitudinal hole through IVDS 31 may be contiguous with a similar hole through the introducer to permit guide wire 39 to be followed to the disk space. Guide wire 39 is placed with introducer tool 300 that is placed into the disc through the space of Kambin. IVDS 31 may be preloaded prior to insertion. That is, IVDS 31 may be compressed to its minimum size as it is attached to introducer tool 300 or before its attachment. Introducer tool 300 may be designed with a more proximal bayonet type latch to secure IVDS 31 to a compressed state. Once inside the disc space, introducer tool 300 is disconnected, allowing IVDS 31 to expand to its desired height as introducer tool 300 is withdrawn. In addition to the space of Kambin, IVDS 31 could be inserted after removing a herniated disc. In this approach, introducer tool 300 could be introduced by direct vision with the operating microscope. Introduction of such a device would be protective against recurrent disc herniations and would recreate a normal disc space height.

In another situation where the patient has undergone multiple posterior decompressions and discectomies, IVDS 31 may be implanted through the abdomen either with an open operation or endoscopy techniques with x-ray guidance.

Figure 4A:
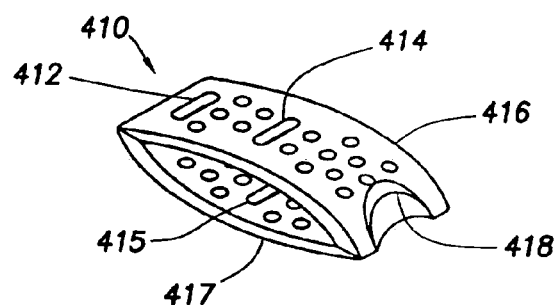
FIG. 4A illustrates an intervertebral disc spacer, having locking sites for engagement with an introducer tool.
Figure 4B:
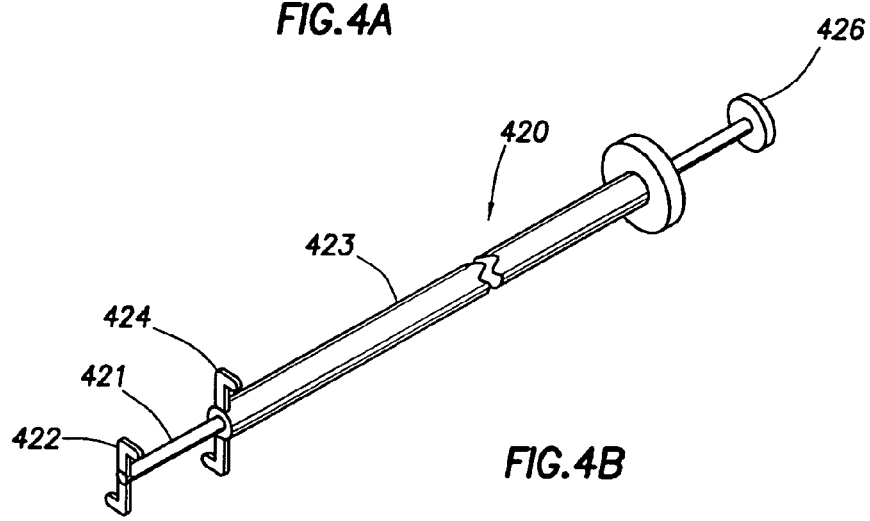
FIG. 4B illustrates an embodiment of an introducer tool for use with certain embodiments of intervertebral disc spacers.
Figure 4C:
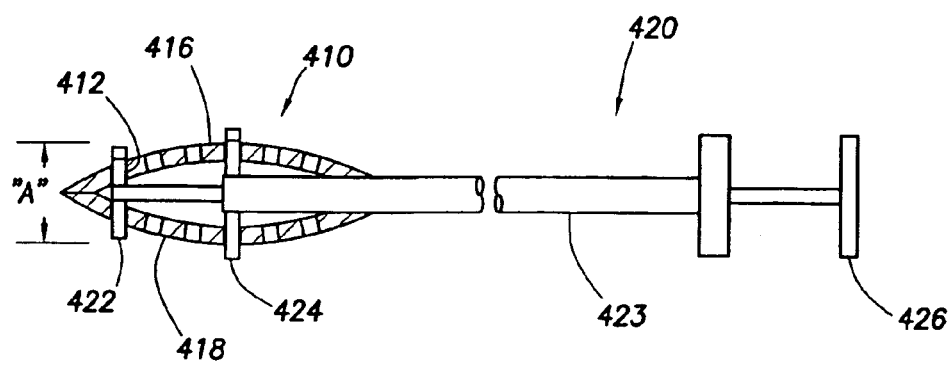
FIG. 4C illustrates an introducer tool in cooperation with an intervertebral disc spacer.

FIG. 4A illustrates another embodiment of an intervertebral disc spacer, having locking sites for engagement with an introducer tool such as the one illustrated in FIG. 4B. FIG. 4C illustrates introducer tool 420 in cooperation with IVDS 410. Introducer tool 420 engages IVDS 410 through port 418. Latching mechanisms 422 and 424 of introducer tool 420 are configured to cooperate with locking sites 412, 414, and 415. That is, latching mechanisms 422 and 424 may be rotated so as to latch onto IVDS 410 through locking sites 412, 414, and 415. Introducer tool 420 is comprised of shaft 421, which telescopes through sleeve 423. Handle 426 may be used to adjust the amount by which shaft 421 projects or telescopes out of sleeve 423. Additionally, handle 426 allows rotation of latching mechanism 422 relative to latching mechanism 424 and sleeve 423. In this way, handle 426 may be used to control the distance between and the relative rotational relation between latching mechanisms 422 and 424.

As shown in FIG. 4C, introducer tool 420 engages IVDS 410 with latching mechanisms 422 and 424. In this embodiment, IVDS 410 is shown in a preloaded or compressed configuration that results in a compressed IVDS height of "A" as shown in FIG. 4C. Preloading IVDS 410 before introducing the device into a patient minimizes the size of the required incisions to insert the apparatus to its final destination. IVDS 410 may be preloaded by compression in a vice, pliers, or any suitable tool for compressing the device to a reduced height.

Figure 4D:
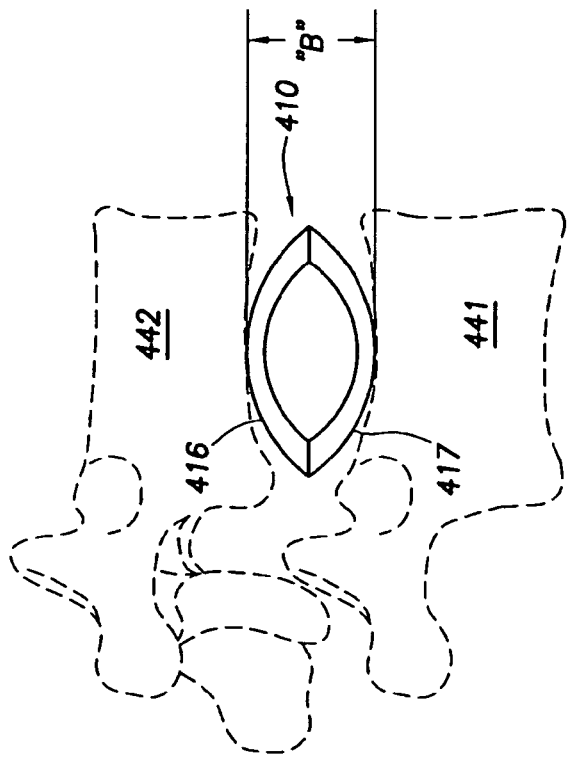
FIG. 4D illustrates an intervertebral disc spacer placed in its environment between two vertebrae.

FIG. 4D illustrates an intervertebral disc spacer placed in its environment between two vertebrae. IVDS 410 is shown placed at its destination between vertebrae 441 and 442. After placement of IVDS 410 and release from introducer tool 420, IVDS 410 is allowed to expand to expanded height "B." In this fashion, IVDS 410 is free to flex between heights "A" and "B" as vertebrae 441 and 442 impose varying forces upon IVDS 410.

FIG. 5A illustrates an exploded view of yet another embodiment of an intervertebral disc spacer comprised of first surface 516 and second surface 517 separated by coiled spring 519. As in FIG. 4A, IVDS 510 has locking sites 512 for engagement with introducer tool 520. Raised surface 518 provides a recessed seat for coiled spring 519 so as to keep coiled spring 519 in place and to prevent coiled spring 519 from ejecting from its placement between first and second surfaces 516 and 517. In certain embodiments, coiled spring 519 may be physically attached to first and second surfaces 516 and 517 by any suitable attachment method including, but not limited to, welding, thermal fusing, compression fusing techniques, or any combination thereof.

FIG. 5B illustrates an exploded view of an embodiment of an intervertebral disc spacer separated by a plurality of springs. IVDS 510 is comprised of first and second surfaces 516 and 517 separated by springs 519. Although IVDS 510 is depicted here with two springs, any suitable number of springs may be used as desired. Further, the springs may be positioned at any desired spacing or intervals along the length of the IVDS 510.

Figure 5D:
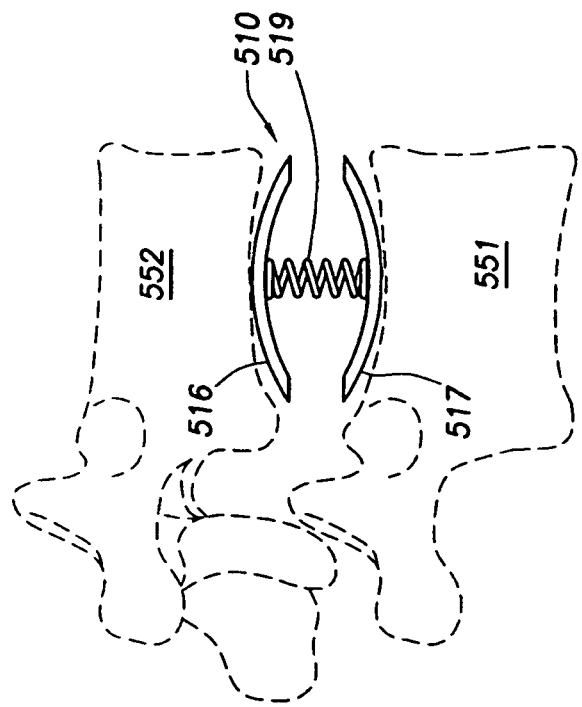
FIG. 5D illustrates an intervertebral disc spacer placed in its environment between two vertebrae.
Figure 5C:
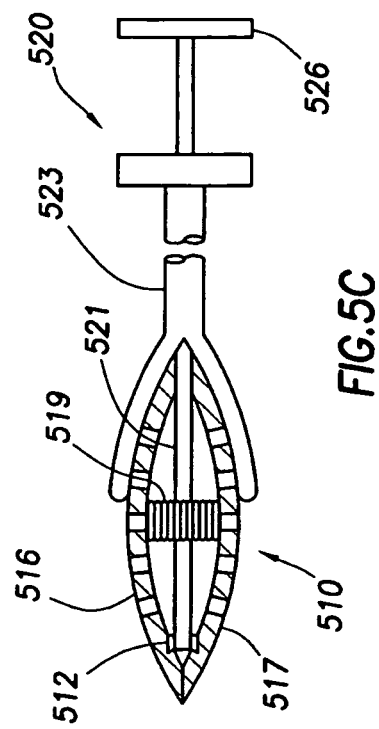
FIG. 5C illustrates an introducer tool in cooperation with an intervertebral disc spacer.

FIG. 5C illustrates an introducer tool in cooperation with an intervertebral disc spacer. Introducer tool 520 engages and maintains IVDS 510 in a compressed state for insertion of IVDS 510 into a patient. As illustrated, coiled spring 519 is capable of bending around introducer stem 521 so as allow passage of introducer stem 521 so that latching mechanisms 512 may engage first and second surfaces 516 and 517 of IVDS 510. FIG. 5D illustrates an intervertebral disc spacer placed in its environment between two vertebrae. Here, IVDS 510 flexes between vertebrae 551 and 552.

Figure 6:
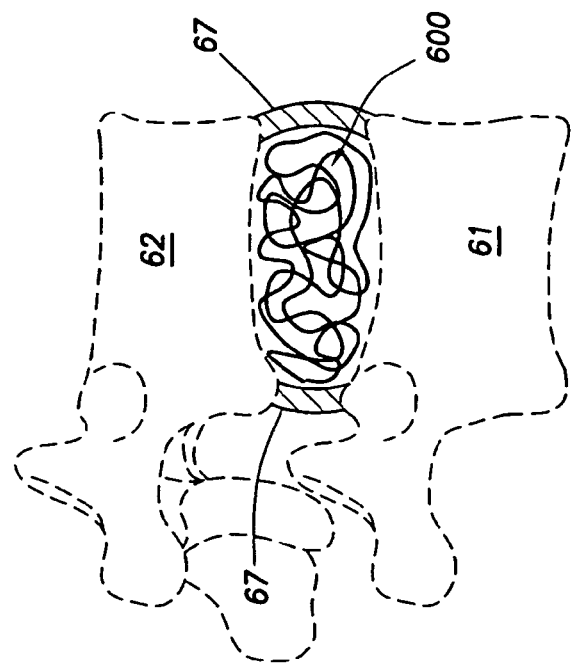
FIG. 6 illustrates a coiled wire disc replacement device placed in its environment between two vertebrae.

FIG. 6 illustrates one embodiment of coiled wire disc replacement device 600 shown here in its environment between two adjacent vertebral end plates 61 and 62 and between annulus fibrosus walls 67. The amount of coiling or spiraling of coiled wire disc replacement device 600 is a function of the material chosen and the desired compressibility of coiled wire disc replacement device 600. The degree of coiling should be chosen so as to optimize the stress distribution of forces imposed by the vertebral end plates. In certain embodiments, the coiling of coiled wire disc replacement device 600 may be uniform so as to substantially form a hollow cylinder.

Suitable diameters of coiled wire disc replacement device 600 include diameters from about 0.5 mm to about 2 mm. Suitable lengths of wire vary from about 30 cm to about several meters, and in some cases up to about 4 m. Examples of suitable materials for coiled wire disc replacement device 600 include, but are not limited to, titanium, nickel/chrome steel, various plastics with adjusted elasticities, synthetic materials such as rubber and silicone, and inert materials known in the art for use as internal prosthetic devices, polyglycolic acid and other absorbable biocompatible materials that may be constructed with suitable material memory characteristics, any of the materials known in the art for joint replacement, or any combination thereof. In certain embodiments, suitable materials have a Young's Modulus (E) of about 10,000,000 to about 19,000,000 and in other embodiments, from about 15,000,000 to about 17,500,000 psi. Suitable metals may deform up to about 3%, 5%, and 7% in certain instances.

Coiled wire disc replacement device 600 may be introduced in the intervertebral space by methods similar to those described above for the various embodiments of the intervertebral disc spacer. In certain embodiments, it may be desirable to attach the loose free ends of coiled spring 600 together so as to prevent the loose free ends from directly impacting adjacent anatomical structures.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

What is claimed is:

1. A method for promoting regeneration of a disc between two adjacent spaced vertebrae of the spinal column normally separated by a disc, the space between the two adjacent vertebrae including a natural disc which is at least partially degenerated, the method comprising:
   a. Introducing an artificial, flexible intervertebral spacer comprising a randomly coiled wire defining a compression spring, wherein the randomly coiled wire is of a length in the range of thirty centimeters to four meters and is of a length sufficient to define a compression spring of sufficient force to simulate the compressive force of a healthy disc, the randomly coiled wire positioned in the space between the two adjacent vertebrae in noninterfering relationship with the at least partially degenerative disc and without disturbing the at least partially degenerated disc, the flexible intervertebral spacer permitting a natural like expansion and compression of the space between the two adjacent spaced vertebrae;
   b. Promoting a proximate normal compression and expansion of the spacer and the at least partially degenerated disc during normal movement of the two adjacent spaced vertebrae;
   c. Stimulating regeneration of the at least partially degenerated disc during normal expansion and compression of the space between the two adjacent spaced vertebrae during normal movement of the two adjacent spaced vertebrae.

2. The method of claim 1, wherein the artificial, flexible intervertebral spacer is a compression spring adapted to simulate the compression force of a natural disc.

3. The method of claim 1, wherein the randomly [compression spring] coiled wire is formed of a material having a Young's Modulus in the range of 15,000,000 to 17,500,000.

4. The method of claim 3, wherein the randomly coiled wire is formed of a titanium compound.

5. The method of claim 1, wherein the randomly coiled wire is deformable to a maximum of approximately 7%.

6. The method of claim 1, wherein the randomly coiled wire is of an outer diameter in the range of 0.5 millimeters to 2 millimeters.

7. The method of claim 1, further including the steps of:
   a. Introducing the randomly coiled wire into the space between the two adjacent vertebrae by inserting a hollow, elongated insertion tool into the body of a subject having an at least partially degenerative disc between the two adjacent vertebrae, and
   b. Advancing the randomly coiled wire into the space through the hollow, elongated insertion tool.

\* \* \* \* \*